(12) United States Patent
Kumazawa et al.

(10) Patent No.: US 7,504,119 B2
(45) Date of Patent: Mar. 17, 2009

(54) PROCESS FOR PRODUCING CHEESE CURD

(75) Inventors: Yoshiyuki Kumazawa, Kawasaki (JP); Noriko Miwa, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 660 days.

(21) Appl. No.: 10/492,208

(22) PCT Filed: Oct. 3, 2002

(86) PCT No.: PCT/JP02/10332

§ 371 (c)(1),
(2), (4) Date: Sep. 15, 2004

(87) PCT Pub. No.: WO03/037094

PCT Pub. Date: May 8, 2003

(65) Prior Publication Data

US 2005/0123645 A1    Jun. 9, 2005

(30) Foreign Application Priority Data

Oct. 31, 2001    (JP) .............................. 2001-335571

(51) Int. Cl.
*A23C 9/12*    (2006.01)
(52) U.S. Cl. .......................... 426/36; 426/34; 426/580; 426/582
(58) Field of Classification Search .................. 426/34, 426/36, 38, 39, 40, 580, 582
See application file for complete search history.

(56) References Cited

U.S. PATENT DOCUMENTS

| 5,681,598 | A | 10/1997 | Kuraishi et al. |
|---|---|---|---|
| 6,093,424 | A | 7/2000 | Han et al. |
| 6,716,461 | B2 | 4/2004 | Miwa et al. |
| 6,749,873 | B2 | 6/2004 | Kumazawa et al. |
| 2003/0054069 | A1 * | 3/2003 | Han et al. ..................... 426/36 |

FOREIGN PATENT DOCUMENTS

| EP | 711504 | 5/1996 |
|---|---|---|
| JP | 2-131537 | 5/1990 |
| WO | 89/07398 | 8/1989 |
| WO | 93 22930 | 11/1993 |

* cited by examiner

*Primary Examiner*—Leslie Wong
(74) *Attorney, Agent, or Firm*—Oblon, Spivak, McClelland, Maier & Neustadt, P.C.

(57) ABSTRACT

In this application is disclosed a process for producing cheese curd characterized in that (a1) a milk-clotting enzyme is added to a raw material milk being kept at a low temperature where the milk protein is not coagulated by the milk-clotting enzyme, whereby the milk-clotting enzyme is allowed to react or work, a transglutaminase is then added, and the resulting mixture is raised in temperature and kept at the raised temperature, whereby the transglutaminase is allowed to react, or (a2) a milk-clotting enzyme and a transglutaminase are simultaneously added to a raw material milk being kept at a low temperature, and the resulting mixture is kept at the same low temperature for a period of time, during which the milk-clotting enzyme is mainly allowed to react, and the resulting mixture is raised in temperature and kept at the raised temperature, during which the transglutaminase is mainly allowed to react, (b) whereby raw material milk curdles, and the resulting coagulated milk is subjected to cutting, followed by separating the whey, whereby cheese curd is obtained, which process is a process according to which inhibition of the reaction of a milk-clotting enzyme by the reaction of a transglutaminase to the milk protein can be avoided, and cheese curd can be obtained in improved yields.

24 Claims, 2 Drawing Sheets

PROCESS FOR PRODUCING CHEESE CURD

CROSS REFERENCES TO RELATED APPLICATIONS

This application is a 371 of International Patent Application No. PCT/JP02/10332, filed on Oct. 3, 2002, and claims priority to Japanese Patent Application No. 2001-335571, filed on Oct. 31, 2001.

TECHNICAL FIELD

The present invention relates to a process for producing cheese curd, more specifically, relates to a process for improving a yield of cheese curd by carrying out an enzyme reaction of a milk-clotting enzyme upon raw material milk at a low temperature in combination with the enzyme reaction of a transglutaminase (occasionally referred to hereinafter simply as "TG"). In addition, the present invention relates to cheese prepared by using cheese curd obtainable by such a way.

BACKGROUND ART

According to an technical committee of FAO, "cheese" is defined as a fresh product or a matured product obtained by coagulating milk, cream, skimmed milk or partially skimmed milk, butter milk, or a partial or total combination of these products, followed by discharging whey ("Dairy product manufacture I," edited by the Editing Committee for Dairy Technology Series Books, 1st ed.; Oct. 30, 1963, Asakura Syoten, Tokyo).

Cheese is roughly classified into natural cheese and processed cheese. The former refers to a fresh product, which has been produced by adding a lactic acid bacterium or a milk-clotting enzyme for curdling, or the matured products thereof. On the other hand, the latter refers to natural cheese which has been processed in such manners wherein the natural cheese is heat-melted and emulsified. Natural cheese is further classified into that produced via a maturing step, such as super hard cheese, hard cheese, semi hard cheese, soft cheese, or the like, and fresh cheese produced without maturing step.

In cheese manufacture, a characteristic step is a curdling step achieved with a milk-clotting enzyme. Naturally, in consideration of the above-described definition of cheese, cheese can be produced by coagulating milk without a milk-clotting enzyme. However, insofar as the present invention is concerned, cheese refers to the one produced by using a milk-clotting enzyme for curdling.

The milk-clotting enzyme is, as known well, called rennet or chymosin which is obtainable by extracting from the abomasum of a calf. In addition, there is rennet derived from other origins such as microorganisms.

A curdling reaction by a milk-clotting enzyme is based on a very fine and sophisticated principle. Milk to be subjected to the curdling reaction (raw material milk) includes bovine milk, goat milk, buffalo milk, reindeer milk, donkey milk, camel milk, and the like. However, not only these whole milk, but also partially skimmed milk, skimmed milk, or powder milks prepared by drying can be used. In each milk, the main component of the protein constituting raw material milk is casein. The reaction of casein caused by a milk-clotting enzyme is an important step for curdling.

Casein is roughly classified into $\alpha$-, $\beta$-, and $\kappa$-caseins and, in milk, $\alpha$- and $\beta$-caseins are localized inside and $\kappa$-casein is localized outside to make a casein micelle structure through calcium. That is, $\kappa$-casein is exposed outside the casein micelle. $\kappa$-Casein is a protein containing a sugar and having a molecular weight of about 19000, and has the hydrophilic portion and the hydrophobic portion. The hydrophobic portion is located inside and the hydrophilic portion is outside, and therefore, the casein micelle exists stable in milk.

The milk-clotting enzyme is a protease having a very high substrate specificity, and cleaves the bond between phenylalanine which is the 105th amino acid and methionine which is the 106th amino acid, both from the N terminal of $\kappa$-casein. This cleaved point is the boundary point between the hydrophilic portion and the hydrophobic portion. Hence, by the enzymatic reaction of the milk-clotting enzyme, the hydrophilic portion is separated from the $\kappa$-casein, and the hydrophobic portion is exposed outside the casein micelle. Individual hydrophobic portions aggregate gradually one another by their interaction to become more instable by the presence of calcium ions, and are precipitated when the temperature is raised. This precipitation is curd, and the water-soluble portion which has not been curdled is separated as whey. The whey fraction contains $\alpha$-lactoalbumin, $\beta$-lactoglobulin, lactose and the like as main components. The curdled fraction is casein and can yield the so-called cheese curd. Cheese curd is subsequently subjected to a salting process to produce natural cheese.

As described above, cheese is yielded by precipitating casein fractions from raw material milk, and therefore, increasing yields thereof is a very important subject from the industrial point of view. Of course, yielding cheese curd in further larger amounts from a certain amount of raw material milk provides higher benefits in various points, including reduction of manufacturing cost, an effective use of milk resources, and providing lower priced products for consumers.

For these reasons, considerable numbers of techniques have been developed to increase the yield of cheese curd. Solving the problem of increasing such yield is closely related to the technical problem of how to incorporate into curd the protein and lactose, which are otherwise discharged as whey.

For example, U.S. Pat. No. 4,205,090 discloses a technique for increasing the yield of cheese curd and, in turn, cheese, using highly concentrated milk by concentration through applying ultrafiltration method. JP-T-1982-501810, a Published Japanese Translation of a PCT Application, discloses a method for preparing cheese by using raw material milk, wherein said raw material milk has been obtained by concentrating selectively a raw material milk by ultrafiltration to increase the ion strength of the raw material milk, followed by fermentation and removal step of the water. In addition, in Japanese Patent Application Laid-open (Kokai) No. 1990-308756 is described that whey yielded as a byproduct upon cheese production is concentrated, and when the resulting concentrated whey protein and a concentrated raw material milk are used to produce cheese, the resulting cheese curd contains the highly concentrated whey protein, which results in the effective use of the whey protein as a byproduct.

However, these techniques require a pretreatment such as ultrafiltration or the like, of raw material milk or whey to be reused, and cannot be said to be convenient industrial methods. In addition, methods of cheese preparation by using raw material milk treated by ultrafiltration causes no effects on the product quality of cheese of a short-term maturation type. However, in the case of cheese of a long-term maturation type, decomposition of the protein and flavor generation of cheese may be inhibited. These defects may be attributable to the facts that, in the case of cheese rich in non-denatured whey protein, the whey protein itself is difficult to decompose, and that the whey protein inhibits decomposition of the casein by a protease (Jameson and Lelierve; Bull. of the IDF, 313: 3-8 (1996), deKoning et al.; Netherlands Milk Dairy J. 35: 35-46 (1981), and Bech; Int. Dairy J. 3: 329-342 (1993)).

In conclusion, the current cheese preparation technique comprising a step of concentrating raw material milk cannot be said to satisfy sufficiently such quality as required by consumers.

On the other hand, in recent years, a cheese preparation technique using a protein-crosslinking enzyme has been reported. The protein-crosslinking enzyme refers herein to a TG. For example, Japanese Patent Application Laid open (Kokai) No. 1989-27471 discloses aproduction example of cheese by using a TG. However, in this case, curdling of milk is carried out not with the milk-clotting enzyme, but by acidification with gluconodeltalactone or lactic acid bacteria and, in addition, it lacks the point "obtainable by discharging whey" described in the definition of cheese made by FAO committee previously mentioned in this description. Therefore, cheese in the case is different from that according to the present invention described in detail later. In addition, in Japanese Patent Application Laid-open (Kokai) No. 1990-131537, a technique of preparing a cheese food by using a TG has been described. The cheese food stated there indicates a processed cheese by using natural cheese as the raw material, and is a food different from natural cheese of the present invention.

WO93/19610 discloses a method wherein a TG is added to an acidic milk protein solution of which the pH has been lowered. However, this method comprises no coagulation step with a milk-clotting enzyme, and therefore, the resultant cheese is different from the natural cheese of the present invention. Also, in WO94/21129 is described a method which comprises using a TG toward an acidic food gel made of a milk protein. However, this method also comprises using no milk-clotting enzyme, and therefore, the resultant cheese is different from the natural cheese of the present invention. WO92/22930 discloses a method of preparation of a milk-like product by using the milk-clotting enzyme, and however, no mention is given of production of cheese itself. In addition, the order in which the milk-clotting enzyme and TG are added to a milk protein solution, which order is one of the essential features of preparation method of cheese curd of the present invention, is never disclosed in this document.

WO94/21130 describes a process for preparing a milk-based non-acidic edible gel, in which a TG is first added to the raw material milk, followed by adding a milk-clotting enzyme, and then the resultant mass is subjected to heating treatment. The heating treatment in this way is a heating treatment at a temperature ranging from 60 to 140° C. after the TG and the milk-clotting enzyme have been added, and this treatment presumably causes the inactivation of the enzyme and formation of the gel. This process comprises no whey separation, which characterizes the inventive cheese preparation, and is remarkably different from the present invention, in the order in which the milk-clotting enzyme and a TG are added and at the temperature range of heating.

On the other hand, WO97/01961 discloses a cheese preparation method in which a TG is added to a raw material milk, followed by adding a milk-clotting enzyme to the resulting mixture, and then the whey is separated. In the description of this disclosure, the TG is reacted at a temperature ranging from 5 to 60° C., preferably from 40 to 55° C. The reaction temperature range of the TG in the cheese curd producing process of the present invention overlaps naturally with that temperature range, because the both temperature ranges are reaction temperature ranges of the same enzyme (TG).

According to the present invention, however, it is an essential element to conduct the κ-casein cleaving reaction with a milk-clotting enzyme, prior to the enzyme reaction with a TG. This element characterizes the production process of the present invention, differing evidently from that disclosed in WO97/01961.

Japanese Patent Application Laid-open (Kokai) No. 1996-173032 describes the method in which (1) a TG is added to a raw material milk to carry out the enzyme reaction for a specific time, followed by carrying out a heating treatment to inactivate the TG, and then, a milk-clotting enzyme is added, (2) a milk-clotting enzyme is added to a raw material milk to carry out the reaction for a specific time, and then, a TG is added, or (3) a milk-clotting enzyme and a TG are added to a raw material milk at the same time. Description is made of conducting the enzymatic reaction with a TG at a temperature ranging from 10 to 40° C. in these steps. However, the method obviously differs from that of the present invention wherein a milk-clotting enzyme is allowed to act at a low temperature.

Further, cheese preparation methods by using a TG include the method disclosed in EP1057411, in which the cheese curd is prepared by adding a TG and a protease which is not rennet (non-rennet protease) to a raw material milk. However, this method is characterized by using a non-rennet protease, and therefore, essentially differs from the cheese curd producing method of the present invention. In addition, EP1057412 discloses the cheese preparation method, in which a TG is added to a raw material milk to carry out the reaction for a certain period of time, followed by adding fat, emulsifier, salt and the like, and the resulting mixture is blended with a cheese solution which has already been heat-dissolved separately. However, this method is a preparation method for processed cheese, and differs from the producing method of the present invention for natural cheese. Moreover, in the above-mentioned EP1057411, a method is described, in which whey is added to a raw material milk, whereby a TG is reacted under the condition wherein the concentration of the whey protein is relatively raised, and then curd is obtainable with a milk-clotting enzyme. However, this method is also completely different from that of the present invention.

Use of a TG in preparing curd for natural cheese may include three methods: (1) a TG is directly added to a raw material milk to carry out the reaction for a certain period of time, and then, a milk-clotting enzyme is added to the reaction mass, (2) a milk-clotting enzyme is added to a raw material milk to carry out the reaction for a certain period of time, and then, a TG is added to the reaction mass, and (3) a milk-clotting enzyme and a TG are added to a raw material milk at the same time.

Among these methods, in the method (1), first, a TG reacts on the protein (casein) in the raw material milk, and next, the milk-clotting enzyme works. The milk-clotting enzyme is, as described above, an enzyme having a very high substrate specificity, and thus, may be decreased in its reactivity to the κ-casein modified with a TG (i.e., the enzymatic reaction is inhibited), in other words, the curdling reaction may be inhibited. Lorenzen (Milchwissenschaft 55 (8): 433-437 (2000)) reported a case wherein curdling performance was much decreased for skimmed milk treated actually with a TG.

Next, in the method (2), first, a milk-clotting enzyme is added to a raw material milk. In this case, a TG is absent during the work of the milk-clotting enzyme, and hence, the enzymatic reaction by the milk-clotting enzyme is not inhibited by a TG. However, as the enzymatic reaction by the milk-clotting enzyme proceeds, the κ-casein is cleaved to separate a glycomacropeptide being the hydrophilic portion, and simultaneously, the hydrophobicity of the surface of the casein micelle increases. This phenomenon means that the curdling reaction goes at the same time, in other words, milk coagulation occurs. Adding a TG after curdling reaction or curd formation has a problem of difficulty in blending the TG uniformly with curd.

Finally, the method (3) is a method in which a milk-clotting enzyme and a TG are added to a raw material milk at the same time. Also in this case, as in the case of the method (1), there is the problem in which the κ-casein modification occurs as the TG reaction proceeds, and then, the curdling reaction by a milk-clotting enzyme is inhibited.

In consideration of the facts as described above, it is not always preferable to use a TG in the curd preparation in natural cheese production in view of inhibition of the curdling reaction (curd formation being inhibited). Inhibition of the curdling reaction by the TG treatment is actually described in WO92/22930 as described above. However, occurrence of a curdling phenomenon requires a specific temperature (around 30° C.) or higher and relates to the calcium concentration in milk, and therefore, it is not always the fact that the TG treatment does not allow preparing natural cheese. In other words, a raw material milk which has been even subjected to a TG treatment can yield curd by raising the temperature or adding calcium.

The techniques of Japanese Patent Application Laid-open (Kokai) No. 1996-173032 and WO97/01961 as described above are techniques using skillfully those techniques, whereby the effect of a TG to inhibit curdling is avoided, and however, there should be an essential solution elsewhere also. Consequently, the problem is how to avoid curdling inhibition of a TG in cheese curd preparation and how to develop a method for adding the TG effectively.

DISCLOSURE OF THE INVENTION

As described above, there is the problem, in which when a TG is allowed to react on milk protein to a certain degree or more, the κ-casein is modified to disturb the reaction of the milk-clotting enzyme on the milk protein, finally resulting in no good formation of curd. Therefore, the problems to be solved by the present invention are how to provide techniques for producing cheese curd, by which curd formation is not disturbed through using a TG, while cheese curd of a good quality is obtainable in good yields by using a TG.

In order to solve the problems as described above, the present inventors have made intensive and extensive research and development. As the result, they have found that the problems as described above can be solved by utilizing the property, by which a raw material milk even subjected to the reaction of a milk-clotting enzyme does not curdle at low temperatures, and combining this with a TG, completed the present invention on the basis of these findings.

Accordingly, the present invention relates to a process for producing cheese curd characterized in that a milk-clotting enzyme is added to a raw material milk or an aqueous solution of a milk protein kept at a low temperature, and the resulting mixture is kept at the same low temperature for a certain period of time, whereby the milk-clotting enzyme is allowed to react or work, a transglutaminase is then added, and the resulting mixture is raised in temperature and kept at the raised temperature for a certain period of time, whereby the transglutaminase is allowed to react and the raw material milk or the aqueous solution of a milk protein curdles in turn, and finally the whey is separated, and also relates to a process for producing cheese curd characterized in that a milk-clotting enzyme and a transglutaminase are simultaneously added to a raw material milk or an aqueous solution of a milk protein being kept at a low temperature, and the resulting mixture is kept at the same low temperature for a certain period of time, during which the milk-clotting enzyme is mainly allowed to react, and the resulting mixture is raised in temperature and kept at the raised temperature for a certain period of time, during which the transglutaminase is mainly allowed to react and the raw material milk or the aqueous solution of a milk protein curdles, and finally the whey is separated.

Here, the reaction of a milk-clotting enzyme at a low temperature (hereafter, referred to as "low temperature renneting") means, specifically, the addition of a milk-clotting enzyme to a raw material milk kept at a low temperature ranging from 0 to 25° C., preferably from 5 to 15° C., whereby the milk-clotting enzyme is allowed to work. In this connection, the curdling reaction by a milk-clotting enzyme is usually carried out under warmed conditions at about 30° C. An advantage of the low temperature renneting method is that a raw material milk can be placed in a standby state for curdling in the state where the reaction to cleave K-casein has been fully progressed by the reaction of an enzyme such as chymosin or the like, and that the raising of the temperature thereafter makes a substantially instant curdling possible. In this way, continuous cheese curd preparation becomes possible. In fact, as continuous curd preparation systems using this method, the Hutin-Stenne system developed in France, the CP system developed for cottage cheese by Crepaco Corporation of USA, and the Nizo system developed in the Netherlands have been practically applied.

TGs are crosslinking enzymes to crosslink proteins and are distributed widely in the nature world. They can crosslink glutamine residues and lysine residues in a protein via the acyl exchange reaction to form a proteinous network structure. It is presumed that the components otherwise originally to be discharged as whey are taken in the reticular structure of the curd, resulting in increase in yields.

According to the present invention, the curd yield is improved, as a result, in such a manner that, at the first step, a milk-clotting enzyme is allowed to react on a raw material milk at a low temperature while keeping the state in which no curdling in fact occurs (hereafter, occasionally referred to as "curdling standby state"), and that, at the second step, a TG is added and the temperature is raised, whereby curdling is caused while crosslinking reaction is caused by a TG in a uniform distribution state of the protein.

The present invention will be described in detail, as flows.

Raw material milk to be used in the process for producing cheese curd of the present invention, is obtainable from animals such as cattles, goats, and the like, and can be in the form of fresh milk, skimmed milk, partially skimmed milk, and processed milk. Fresh milk means milk remaining intact after milking, skimmed milk means fresh milk from which almost all the milk fat content has been removed, partially skimmed milk means fresh milk from which the milk fat content has been removed, except for skimmed milk, and processed milk means what is prepared by processing fresh milk, skimmed milk, partially skimmed milk, or the like. In addition, the aqueous solution of a milk protein, which has been prepared by dissolving in water, powder milk (whole milk powder, skimmed milk powder, instant milk powder, modified milk powder), or the like, can be also used as the raw material for the process for producing cheese curd of the present invention.

For the process for producing cheese curd of the present invention, TGs can be used regardless of the origin thereof, insofar as they can catalyze the acyl exchange reaction between the gamma carboxy-amide group of a glutamine residue and the epsilon amino group of a lysine residue, which are present in the protein. Examples thereof include that derived from Actinomyces bacteria (Japanese Patent No. 2572716), that derived from *Bacillus subtillis* (Japanese Patent Application Laid-open (Kokai) No. 1999-137254), that derived from guinea pig liver (Japanese Patent No. 1689614), that derived from oyster (U.S. Pat. No. 5,736,356), and the like. In addition, those prepared by gene recombination can be naturally used. Among them, the TG most easy to use is the enzyme derived from Actinomyces bacteria (the above-mentioned Japanese Patent No. 2572716) in consideration of relatively heat-stable, low substrate specificity, and possible stable supply.

Concerning the activity of a TG to be used for the production process of the present invention, in the case where benzyl oxycarbonyl-L-glutaminyl-glycine and hydroxylamine are used as the substrate, 1 unit is defined as the activity to produce 1 micromole of the reaction product for 1 minute at 37° C. (hydroxamate method). However, as described above, TGs are derived from various origins, and the activity thereof can not be always determined by applying this definition. Even in such case, an amount showing substantially the predetermined effect of the present invention falls in a range of TGs to be added according to the present invention, and also falls naturally in the scope of the present invention.

A milk-clotting enzyme to be used for the process for producing cheese-curd of the present invention, is not restricted to a specific origin. Usable examples include calf rennet used most commonly, and also those such as bovine rennet, swine pepsin, fowl rennet, sheep rennet and goat rennet, which are derived from animal origins, those derived from the genus Mucor, originated from microorganisms, those derived from plants, those produced by gene recombination, and the like.

At the first step of the process of the present invention, a raw material milk or an aqueous solution of a milk protein (in the following description, both being represented by a raw material milk) is added with a milk-clotting enzyme at a low temperature ranging from 0 to 25° C., preferably from 5 to 15° C., while the mass is being kept at such a low temperature, whereby the reaction of cleaving κ-casein is caused to occur (low temperature renneting). Reaction time depends on the reaction temperature and ranges from 15 minutes to 6 hours, preferably from 30 minutes to 3 hours. In the inventive low temperature renneting, the reaction mixture may be indeed permitted to stand for a long time (for example, overnight), which is different from ordinary renneting. Further, if required (for example, in the case of such fresh cheese as "quark", fermentation can be conducted by adding a lactic acid bacterial starter at the same time. This is because though the pH of the raw material milk is gradually lowered by the fermentation, the optimum pH for the reaction of a milk-clotting enzyme is located in the acidic condition, and therefore, the enzymatic reaction of the milk-clotting enzyme is not inhibited by such fermentation.

Subsequently, at the second step, a TG is added to work on the raw material milk on which the milk-clotting enzyme has been allowed to react. The TG is added in an amount ranging, in view of ordinary enzyme-substrate reaction, from 0.1 to 50 units, preferably from 0.5 to 20 units per 1 g of the protein present in the raw material milk. The addition amount of less than 0.1 units provides no desired, intended effect by a TG. On the other hand, the addition amount of a TG of more than 50 units makes the reaction proceed acutely and excessively, resulting in a possible bad effect on the quality of the resultant curd.

At the stage of this TG addition, as described above, the raw material milk has indeed been reacted by the milk-clotting enzyme but is kept at the low temperature, and therefore, no curdling has occurred, whereby the mass or reaction mixture is kept in a solution state (curdling standby state). Consequently, the TG can be surely uniformly dispersed in the raw material milk.

After a TG has been added and dissolved, the manipulation of raising the temperature is started subsequently. The temperature of the raw material milk, after the temperature has been raised, is naturally an appropriate temperature ordinarily suitable for the expression of the enzymatic reaction of the TG, whereby the crosslinking reaction starts. A raising rate of the temperature is not particularly restricted, when it is practically possible. The crosslinking reaction by a TG is an enzymatic reaction, and thus, the amount of the reaction depends on the temperature and time. Usually, the intended effect of the present invention can be sufficiently realized by keeping a reaction mixture at a temperature ranging from 25 to 60° C., preferably from 30 to 50° C. for 10 minutes to 3 hours, preferably 20 minutes to 1 hour (time from the temperature raising to the start of the operation of whey separation). These are referred to Example 1 mentioned later.

Incidentally, any curdling does not occur at the first step of the present invention, wherein a milk-clotting enzyme is added to a raw material milk kept at a low temperature. Therefore, when a TG is added at the low temperature, it can be dispersed uniformly in the raw material, as has been described above. Moreover, at low temperatures, the κ-casein is modified by the TG to a small degree, whereby the reaction by the milk-clotting enzyme may not be inhibited. In other words, at low temperatures, a milk-clotting enzyme and a TG can be added at the same time. And, when the temperature is raised, whereby the enzymatic reaction of the TG is expressed, curdling is caused to occur. These are referred to Example 2 mentioned later.

The operations or manipulations following the crosslinking reaction by a TG are not specially restricted, but ordinary ones can be employed, such as curd cutting and whey separation, followed by producing various kinds of natural cheese from the cheese curd obtained.

According to the present invention, as described above, a raw material milk is subjected to renneting at a low temperature, whereby it keeps a solution state (curdling standby state) in spite of the milk-clotting enzyme having been allowed to react thereon. If a TG is added to, and is allowed to react on the raw material milk, cheese curd can be prepared without any inhibition of the renneting. And, the target cheese curd is obtainable in higher yields, because the protein is crosslinked by the TG (reticular structure of the protein having been formed by crosslinking), whereby the components (α-lactoalbumin, β-lactoglobulin, lactose and the like) originally otherwise to be separated as whey are held therein and also, the water holding capacity is improved.

Figure 1:
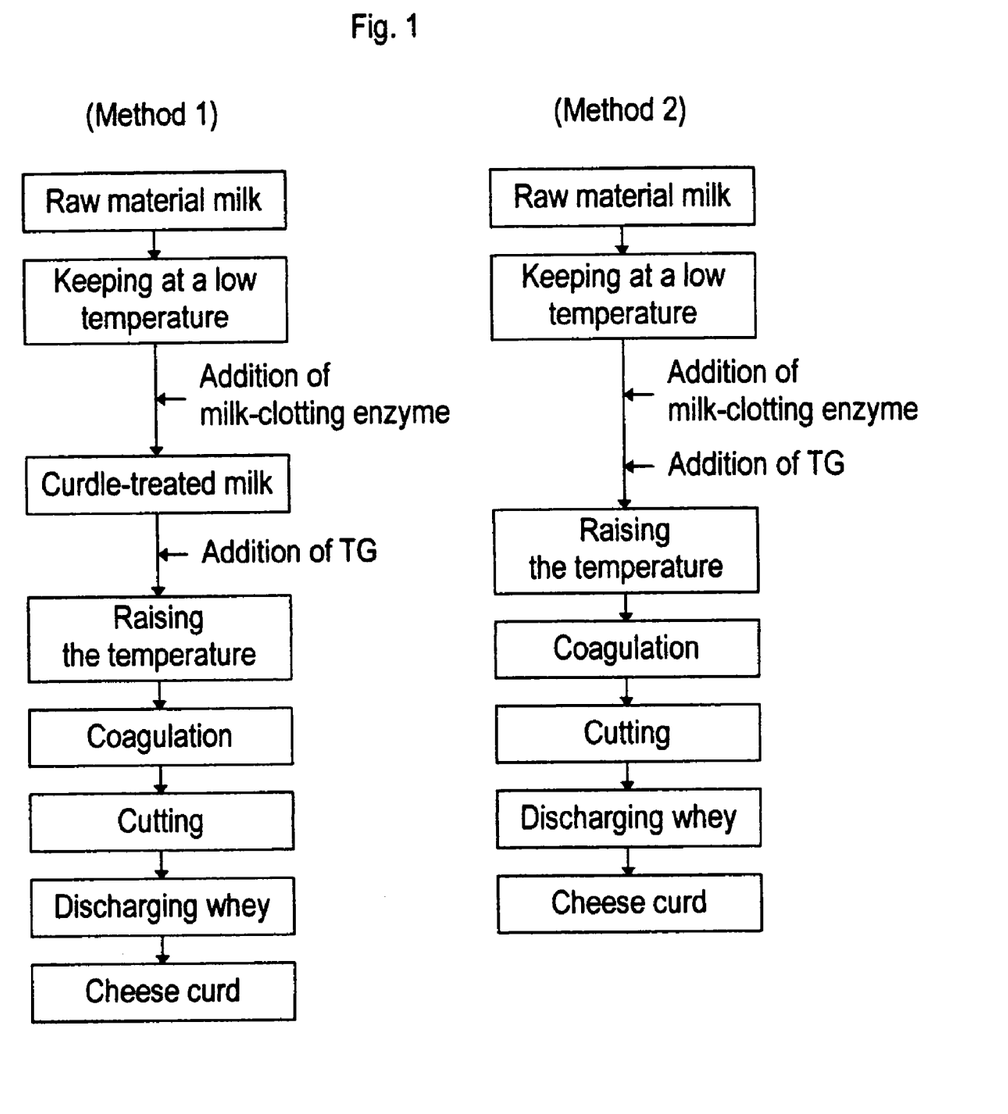
FIG. 1 illustrates the steps of producing cheese curd with the use of a TG, utilizing the low temperature renneting.

FIG. 1 will show an outline of the process for producing cheese curd, according to the present invention as described above.

BEST MODE FOR CARRYING OUT THE INVENTION

The invention will be further described in detail as follows with reference to Test Examples and Examples. In the following Test Examples and Examples, the amount of a TG (to be) added is abbreviated as unit(s)/g, for the number of units (to be) added per 1 g of the milk protein.

TEST EXAMPLE 1

Inhibition of Renneting by a TG

In the first place, a Test Example is shown to indicate a decrease in curdling performance caused by the TG treatment.

A TG preparation (ex Ajinomoto Co., Inc., specific activity: 1,000 units/g) derived from an Actinomyces was added in an amount of 0, 2, 5, 8, 10, or 20 units/g to a 1 L portion of a raw material milk (sterilized at 63° C. for 30 min.), which had been set at a constant temperature of 25° C. or 37° C., followed by carrying out the enzymatic reaction by the TG for 2 hours. Subsequently, the TG was inactivated by heating once to 75° C., followed by cooling to 32° C., and then, rennet ("Standard Plus 900" ex Christian-Hansen Corp.) was added in such amount that it would be in an amount of 0.003 wt. percent of the raw material milk, and the resulting mixture was kept at the temperature for 1 hour. After these steps, the coagulated state was observed, and the coagulated or curdled products were subjected to cutting, centrifugation at 3,000 rpm for 10 min., whereby the curd was separated from the whey. The results are presented in the following Table 1. In the Table, the curd weight represents a wet weight of the curd after the whey was removed. And, the curd yield represents a relative value to the curd weight in the case of no addition of the TG.

TABLE 1

| Temp. (° C.) | TG (U/g) | Coagulated state | Whey amount (mL) | Protein in the whey (mg) | Curd weight (g) | Curd yield (%) |
|---|---|---|---|---|---|---|
| 37 | 0 | Coagulated | 479 | 967 | 511 | 100 |
| 37 | 2 | Not coagulated | — | — | 0 | 0 |
| 37 | 5 | Not coagulated | — | — | 0 | 0 |
| 37 | 8 | Not coagulated | — | — | 0 | 0 |
| 37 | 10 | Not coagulated | — | — | 0 | 0 |
| 37 | 20 | Not coagulated | — | — | 0 | 0 |
| 25 | 0 | Coagulated | 488 | 973 | 515 | 100 |
| 25 | 2 | Loosely coagulated | 463 | 810 | 507 | 98.4 |
| 25 | 5 | Very loosely coagulated | 525 | 2,278 | 461 | 89.5 |
| 25 | 8 | Not coagulated | — | — | 0 | 0 |
| 25 | 10 | Not coagulated | — | — | 0 | 0 |
| 25 | 20 | Not coagulated | — | — | 0 | 0 |

As shown in Table 1, in respect of the milk portions subjected to the enzymatic reaction by the TG at 37° C., no curdling reaction of the milk by the rennet was observed. On the other hand, in respect of the milk portions subjected to the reaction at 25° C., coagulation was observed when the TG was added in an amount of 5 or smaller units/g. However, in respect of the mass when it was added in an amount of 5 units/g, the supernatant after centrifugation showed in fact a very whitely turbid state, suggesting an inhibited curdling reaction. The whitely turbid state may be caused by the casein, which had not been involved in curdling or coagulating, remained in the supernatant in consideration of a very large amount of the protein in the supernatant. In the case of the 2 units/g addition, curdling was indeed observed, but it was evidently loose in comparison with the case of no addition of the TG. These results show that as the enzymatic reaction of the TG proceeds, coagulation gets difficult to occur, which, in turn, suggests that the κ-casein modification by the TG causes the enzymatic reaction by the milk-clotting enzyme to get difficult to occur.

TEST EXAMPLE 2

Inhibition by the TG Treatment of the Formation of Glycomacropeptide

In the next place, quantitative determination of glycomacropeptide as the reaction product by the milk-clotting enzyme was actually attempted.

First, calcium chloride was added to a 50 mL portion of a raw material milk (sterilized at 63° C. for 30 min.) in such that it would be in an amount of 0.05 wt. percent of the milk, and the mixture was set to a constant temperature of 30° C. Subsequently, a TG was added to the raw material milk in such that it would be in an amount of 5 units/g, followed by allowing the enzymatic reaction by the TG for 1 hour. Following this step, rennet was added in such that it would be in an amount of 0.003 wt. percent of the raw material milk. Sampling was made time-wise, and the specimens were subjected to reverse high speed liquid chromatography. The chromatogram obtained was used for quantifying a peak of the glycomacropeptide. The result will be shown in FIG. 2 (with TG treatment). The quantification was conducted in the same way, except for no addition of the TG for comparison. The result will be also shown in FIG. 2 (without TG treatment).

Figure 2:
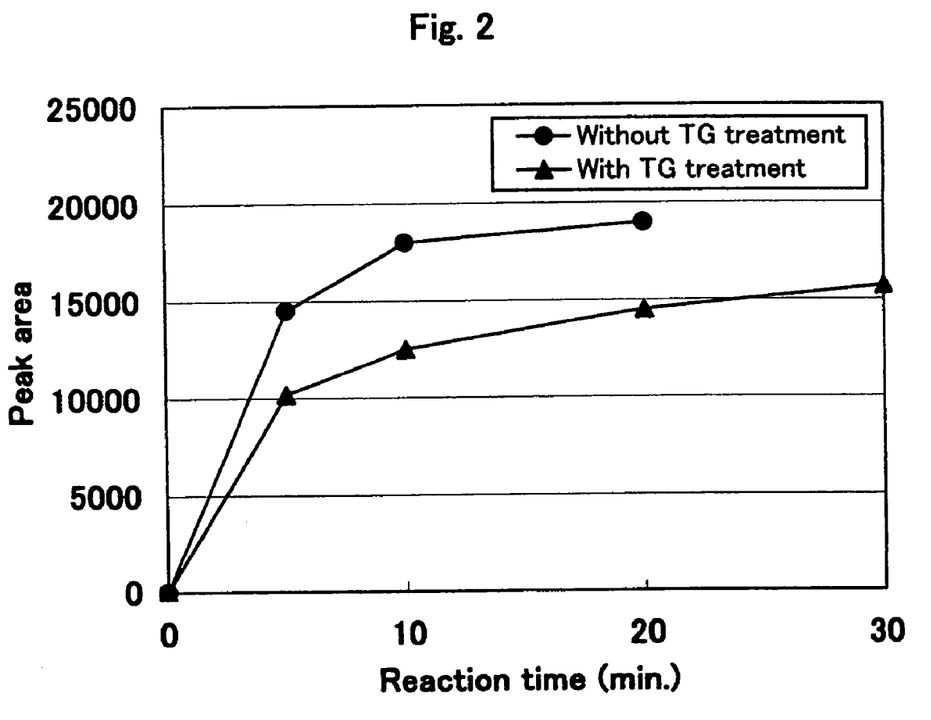
FIG. 2 shows the result of quantitative determination of the glycomacropeptide by high speed liquid chromatography (Test Example 2).

As can be understood from FIG. 2, regardless of the presence or absence of the TG, the amount of the glycomacropeptide generated in the raw material milk showed an increasing tendency with the passage of time. In the case of no addition of the TG (without TG treatment), the amount of the glycomacropeptide generated after rennet was added, increased abruptly until about 10 minutes after, and reached an almost maximum amount after about 20 minutes. On the other hand, in the case of addition of the TG (with TG treatment), the increase of the glycomacropeptide generated was obviously slow in comparison with the case of no addition of the TG, while tending to be moderate until about 30 minutes after the adding operation. This result shows clearly that the generation of glycomacropeptide was inhibited by the addition of the TG, suggesting that the raw material milk subjected to the TG treatment becomes difficult to be subjected to the reaction of the milk-clotting enzyme.

TEST EXAMPLE 3

Inhibition of Coagulation by a Low Temperature Renneting

In the third place, observation was made for a relationship between temperatures and the coagulated state of milk.

To ten 1 L portions of a raw material milk (sterilized at 63° C. for 30 min.), calcium chloride was not added or added in such that it would be in an amount of 0.05 wt. percent, and the individual mixtures were kept at 10, 15, 25, 32 or 37° C. Following this step, rennet was added in such that it would be in an amount of 0.03 wt. percent of the raw material milk, whereby curdling reaction was conducted, and the coagulated state of the milk was observed after 60 minutes. The result will be shown in the following Table 2.

TABLE 2

| CaCl$_2$ (%) | Temp. (° C.) | Coagulated state |
| --- | --- | --- |
| 0.05 | 10 | Not coagulated |
| 0.05 | 15 | Not coagulated |
| 0.05 | 25 | Coagulated |
| 0.05 | 32 | Coagulated |
| 0.05 | 37 | Coagulated |
| 0 | 10 | Not coagulated |
| 0 | 15 | Not coagulated |
| 0 | 25 | Not coagulated |
| 0 | 32 | Coagulated |
| 0 | 37 | Coagulated |

As can be understood from Table 2, in the case of addition of the calcium chloride, coagulation of the milk was not observed at a temperature of 15° C. or lower. On the other hand, in the case of no addition of the calcium chloride, coagulation of the milk was not observed at a temperature of 25° C. or lower. From these results, it has been confirmed that addition and action of the rennet, which is a milk-clotting enzyme, inhibited surely milk coagulation at the low temperatures, and the masses remained to keep a solution state.

EXAMPLE 1

Improving Yields of Cheese Curd by a TG
(Method 1 of FIG. 1)

To four 1 L portions of the raw material milk (sterilized at 63° C. for 30 min.) while kept at 15° C., rennet was added in such that it would be in an amount of 0.003 wt. percent of the raw material milk. At the 60th minute after the rennet was added, a TG was added in such that it would be in an amount of 0, 2, 5 or 10 units/g. The resulting mixtures were stirred well, followed by raising the temperature thereof to 32° C., and were kept at the temperature for 60 minutes, whereby the TG was allowed to react. Following this step, the coagulated milk was subjected to cutting and centrifugation at 3,000 rpm for 10 min., whereby the curd was separated from the whey.

The wet weight of the obtained curds was measured, and the relative values to the value in the case of no addition of the TG was calculated (curd yield), whereby the increase thereof was observed. In addition, the water was removed from the curds by freeze-drying, the dry weight of the curds was measured, and further, the relative values to the value in the case where the TG was not added, were calculated (solid content yield). The result will be presented in the below-mentioned Table 3.

As the result, as can be understood from the table, as the concentration of the TG added, was increased, both the wet weight and the yield of the curds were increased, presenting a 17 percent increase in the case of 10-unit TG/g in comparison with the case of no TG addition. In addition, the solid content yields showed an increase. These results show evidently a possibility of improving curd yields by combination of a low temperature rennetting with a TG. At this time, the increase in the solid content yields was also observed and, therefore, it was suggested that not only the water-holding capacity of curd but also components such as lactose otherwise inherently discharged to the whey being taken in the curd, may occur.

TABLE 3

| TG (U/g) | Wet curd weight (g) | Curd yield (%) | Dried curd weight (g) | Solid content yield (%) |
| --- | --- | --- | --- | --- |
| 0 | 401 | 100 | 85.5 | 100 |
| 2 | 429 | 107 | 87.5 | 102 |
| 5 | 456 | 114 | 88.8 | 104 |
| 10 | 468 | 117 | 89.8 | 105 |

EXAMPLE 2

Improving Yields of Cheese Curd by a TG
(Method 2 of FIG. 1)

To our 1 L portions of a raw material milk (sterilized at 63° for 30 min.) while kept at 15° C., rennet was added in such that it would be in a amount of 0.003 wt. percent of a raw material milk and, at the same time, a TG was added in such that it would be in an amount of 0, 2, 5 or 10 units/g, and the individual mixtures were stirred well. Following keeping the temperature thereof at 15° C. for 60 minutes, the temperature thereof was raised to 32° C., and the mixtures were kept at this temperature for 60 minutes, whereby the TG was allowed to react. Following this step, the coagulated milk was subjected to cutting and centrifugation at 3,000 rpm for 10 min. to separate the curd from the whey.

The wet weight of the obtained curds was measured, and the relative values to the value in the case of no addition of the TG was calculated (curd yield), whereby the increase thereof was observed. In addition, the water was removed from the curds by freeze-drying, the dry weight of the curds was measured, and further, the relative values to the value in the case where the TG was not added, were calculated (solid content yield). The result will be presented in the below-mentioned Table 4.

As the result, as can be understood from the table, as the concentration of the TG added, was increased both the wet weight and the yield of the curds were increased, presenting a 15 percent increase in the case of 10-unit TG/g in comparison with the case of no TG addition. In addition, the dry weight showed an increase. Further, the solid content yields showed an increase. These results show that almost the same effect as that of the case of Example 1 (method 1), can be expected. Concerning the increase in the solid content yields, the improvement in the curd yields suggests, as the same as in the above-described method 1, the increase in the water-holding capacity and taking-in of the lactose and the like in the curd.

TABLE 4

| TG (U/g) | Wet curd weight (g) | Curd yield (%) | Dried curd weight (g) | Solid content yield (%) |
| --- | --- | --- | --- | --- |
| 0 | 399 | 100 | 86.8 | 100 |
| 2 | 430 | 108 | 87.8 | 101 |
| 5 | 433 | 109 | 87.5 | 101 |
| 10 | 460 | 115 | 88.5 | 102 |

EXAMPLE 3

Improving Yields of Fresh Cheese by Applying Low Temperature Renneting

Four 5 L portions of a raw material milk (sterilized at 63° for 30 min.) were each treated by heating to about 85° C. for sterilization. The raw material milk portions were cooled to 15° C., followed by adding a lactic acid bacteria starter ("YoFlex Y370" ex Christian-Hansen Corp.), rennet, and calcium chloride in amounts of 0.02 percent, 0.003 percent, and 0.01 percent, respectively. The resulting mixtures were well blended by stirring. Subsequently, the portions were then added with the TG in such that it would be in amounts of 0, 2, 5 and 10 units/g, respectively, and kept at 21° C. for 26 hours, whereby fermentation was allowed to proceed. Following this step, the coagulated raw material milks were warmed and kept at 55° C. for 2 minutes for efficient whey discharge. Subsequently, the masses were cooled to 30° C., and subjected to cutting. The four curds were collected with gauze and suspended in a refrigerator overnight, whereby the whey was discharged. Each resulting curd was added with table salt in such that it would be in an amount of 1 wt. percent of the curd, and kneaded well, whereby fresh cheese was prepared.

In respect of the four kinds of yielded fresh cheese, the following Table 5 shows the weight, the yield (relative value to the value in the case where the TG was not added), water removal and the evaluated taste on the 3rd day after production. As the result, in accordance with the increased TG amount added, the weight of the yielded fresh cheese increased, and addition of 10 units/g of the TG showed an improved 27 percent of the yield. The product, to which the TG had not been added, showed water removal after preservation for 3 days. However, adding the TG suppressed water removal. Regarding the texture, the product showed a slightly dried crumbling feeling, lacking creamy feeling, in the case where the TG was not added. However, in the case where the TG was added, the products had a mild mouth feeling and creamy feeling. Addition of 10 units/g of the TG provided a slightly sloppy feeling, but no organoleptic problem.

TABLE 5

| TG (U/g) | Weight (g) | Yield (%) | Water removal | Texture |
|---|---|---|---|---|
| 0 | 1,090 | 100 | Slight | Slightly dried crumbling feeling, Lacking creamy feeling |
| 2 | 1,179 | 108 | None | Mild mouth feeling Creamy feeling |
| 5 | 1,266 | 116 | None | Mild mouth feeling Creamy feeling |
| 10 | 1,384 | 127 | None | Mild mouth feeling, Slightly sloppy feeling |

Incidentally, the above-mentioned Japanese Patent Application Laid-open (Kokai) No. 1996-173032 discloses an example of preparation of cheese curd at an ordinary temperature renneting (around 30° C.) and mentions that regarding an evaluation system for a fresh cheese ("Quark"), the addition of 5 units/g of a TG showed 13 percent increase in the yield, and regarding an evaluation system for cheddar cheese, the addition of 10 units/g of a TG showed 19 percent increase in the yield. In comparison with these results, the process of the present invention can provide, as described in the above-mentioned Table 5, the addition of 5 units/g of the TG showed 16 percent increase in the yield, and the addition of 10 units/g of the TG showed 27 percent increase, showing evidently high yields.

INDUSTRIAL APPLICABILITY

According to the invention, inhibition of the reaction of a milk-clotting enzyme by the reaction of a transglutaminase to a milk protein can be avoided, whereby a process for producing cheese curd in improved yields is provided.

The invention claimed is:

1. A process for producing cheese curd, which comprises:
   adding a milk-clotting enzyme to a raw material milk or an aqueous solution of a milk protein being kept at a low temperature of from 0° C. to 25° C., wherein the resulting mixture is kept at the same low temperature for a period of time from 15 minutes to 6 hours, whereby the milk-clotting enzyme is allowed to react or work,
   adding a transglutaminase; wherein the resulting mixture is raised in temperature to from 25 ° C. to 60 ° C. and kept at the raised temperature for a period of time from 10 minutes to 3 hours, whereby the transglutaminase is allowed to react and the raw material milk or the aqueous solution of a milk protein curdles in turn, and finally
   separating the whey.

2. A process for producing cheese curd, which comprises:
   simultaneously adding a milk-clotting enzyme and a transglutaminase to a raw material milk or an aqueous solution of a milk protein being kept at a low temperature of from 0° C. to 25° C., wherein the resulting mixture is kept at the same low temperature for a period of time from 15 minutes to 3 hours, during which the milk-clotting enzyme is mainly allowed to react, and wherein the resulting mixture is raised in temperature to from 25° C. to 60° C. and kept at the raised temperature for a period of time from 10 minutes to 3 hours, during which the transglutaminase is mainly allowed to react and the raw material milk or the aqueous solution of a milk protein curdles, and finally
   separating the whey.

3. The process of claim 1, wherein said low temperature is from 5° C. to 15° C.

4. The process of claim 1, wherein said raw material milk is obtained from cattle or goats.

5. The process of claim 1, wherein said raw material milk is selected from the group consisting of fresh milk, skimmed milk, partially skimmed milk, and processed milk.

6. The process of claim 1, wherein said milk-clotting enzyme is calf rennet.

7. The process of claim 1, wherein said milk-clotting enzyme is selected from the group consisting of bovine rennet, swine pepsin, fowl rennet, sheep rennet and goat rennet.

8. The process of claim 1, wherein said milk-clotting enzyme is selected from the group consisting of a milk-clotting enzyme from the genus Mucor and a plant-derived milk-clotting enzyme.

9. The process of claim 1, wherein said resulting mixture is kept at the same low temperature for a period of time from 30 minutes to 3 hours.

10. The process of claim 1, wherein said transglutaminase is added at an amount ranging from 0.1 to 50 units per 1g of the protein present in the raw material milk.

11. The process of claim 1, wherein said transglutaminase is added at an amount ranging from 0.5 to 20 units per 1g of the protein present in the raw material milk.

12. The process of claim 1, wherein the temperature of said raised in temperature ranges from 30° C. to 50° C.

13. The process of claim 1, wherein said kept at the raised temperature for a period of time is from 20 minutes to 1 hour.

14. The process of claim 2, wherein said low temperature is from 5° C. to 15° C.

15. The process of claim 2, wherein said raw material milk is obtained from cattle or goats.

16. The process of claim 2, wherein said raw material milk is selected from the group consisting of fresh milk, skimmed milk, partially skimmed milk, and processed milk.

17. The process of claim 2, wherein said milk-clotting enzyme is calf rennet.

18. The process of claim 2, wherein said milk-clotting enzyme is selected from the group consisting of bovine rennet, swine pepsin, fowl rennet, sheep rennet and goat rennet.

19. The process of claim 2, wherein said milk-clotting enzyme is selected from the group consisting of a milk-clotting enzyme from the genus Mucor and a plant-derived milk-clotting enzyme.

20. The process of claim 2, wherein said resulting mixture is kept at the same low temperature for a period of time from 30 minutes to 3 hours.

21. The process of claim 2, wherein said transglutaminase is added at an amount ranging from 0.1 to 50 units per 1g of the protein present in the raw material milk.

22. The process of claim 2, wherein said transglutaminase is added at an amount ranging from 0.5 to 20 units per 1g of the protein present in the raw material milk.

23. The process of claim 2, wherein the temperature of said raised in temperature ranges from 30° C. to 50° C.

24. The process of claim 2, wherein said kept at the raised temperature for a period of time is from 20 minutes to 1 hour.

* * * * *

UNITED STATES PATENT AND TRADEMARK OFFICE
CERTIFICATE OF CORRECTION

PATENT NO. : 7,504,119 B2
APPLICATION NO. : 10/492208
DATED : March 17, 2009
INVENTOR(S) : Yoshiyuki Kumazawa et al.

It is certified that error appears in the above-identified patent and that said Letters Patent is hereby corrected as shown below:

Column 3, line 13, "discloses aproduction example of"
    should read -- discloses a production example of --.

Column 11, line 6, "in an amount of 0.03 wt. percent"
    should read -- in an amount of 0.003 wt. percent --.

Column 12, line 22, "To our 1 L portions of a raw material milk (sterilized at 63°"
    should read -- To four 1 L portions of a raw material milk (sterilized at 63° C --.

Column 13, line 6, "Four 5 L portions of a raw material milk (sterilized at 63°"
    should read -- Four 5 L portions of a raw material milk (sterilized at 63° C --.

Signed and Sealed this

Eighteenth Day of August, 2009

David J. Kappos
*Director of the United States Patent and Trademark Office*